(12) United States Patent
Luna et al.

(10) Patent No.: US 7,192,781 B2
(45) Date of Patent: Mar. 20, 2007

(54) METHODS FOR STABILIZING 5-AZACYTIDINE IN PLASMA

(75) Inventors: Marsha Luna, Shawnee, KS (US); Larry Eden, Overland Park, KS (US); Steven Burmaster, Lee's Sumitt, MO (US)

(73) Assignee: Pharmion Corporation, Boulder, CO (US)

( * ) Notice: Subject to any disclaimer, the term of this patent is extended or adjusted under 35 U.S.C. 154(b) by 274 days.

(21) Appl. No.: 10/823,394

(22) Filed: Apr. 13, 2004

(65) Prior Publication Data

US 2005/0227367 A1 Oct. 13, 2005

(51) Int. Cl.
*G01N 33/00* (2006.01)
*G01N 1/18* (2006.01)

(52) U.S. Cl. .......................... 436/98; 436/63; 436/106; 436/161; 436/173; 436/174; 436/177; 436/178

(58) Field of Classification Search .................. 436/45, 436/63, 92, 98, 106, 161, 173, 174, 177, 436/178, 181

See application file for complete search history.

(56) References Cited

U.S. PATENT DOCUMENTS 6,943,249 B2 9/2005 Ionescu et al.

OTHER PUBLICATIONS

J.A. Beisler (1978) J. Med. Chem. 21:204-208.
Kornblith et al. (2002) J. Clin. Oncol. 20:2441-2452.
Silverman et al. (2002) J. Clin. Oncol. 20:2429-2440.
Rustum & Hoffman (1987) J. Chromatog. 421:387-391.

*Primary Examiner*—Maureen M. Wallenhorst
(74) *Attorney, Agent, or Firm*—Swanson & Bratschun, LLC

(57) ABSTRACT

The invention provides methods for stabilizing 5-azacytidine against hydrolysis in plasma. By extracting the 5-azacytidine into acetonitrile and zinc sulfate, the 5-azacytidine can be stored for at least about 3 hours at about room temperature, and for at least about 4 days at about −70° C. If the acetonitrile is removed and evaporated to dryness, the 5-azacytidine in the resulting residue is stable for at least about 14 months at about −70° C. The invention also provides methods for determining the 5-azacytidine in acetonitrile, or in the acetonitrile residue, using, for example, high-performance liquid chromatography. The methods of the invention permit a significant time interval between the initial processing of the whole blood sample and the time of 5-azacytidine determination.

8 Claims, 1 Drawing Sheet

METHODS FOR STABILIZING 5-AZACYTIDINE IN PLASMA

FIELD OF THE INVENTION

This invention is directed to methods for stabilizing 5-azacytidine in plasma. The invention is also directed to methods for determining the concentration of 5-azacytidine in plasma.

BACKGROUND OF THE INVENTION

5-Azacytidine (also known as azacitidine and 4-amino-1-β-D-ribofuranosyl-1,3,5-triazin-2(1H)-one; Nation Service Center designation NSC-102816; CAS Registry Number 320-67-2) has undergone NCI-sponsored trials for the treatment of myelodysplastic syndromes (MDS). See Kornblith et al., J. Clin. Oncol. 20(10): 2441–2452 (2002) and Silverman et al., J. Clin. Oncol. 20(10): 2429–2440 (2002). 5-Azacytidine may be defined as having a molecular formula of $C_8H_{12}N_4O_5$, a relative molecular weight of 244.20 and a structure of:

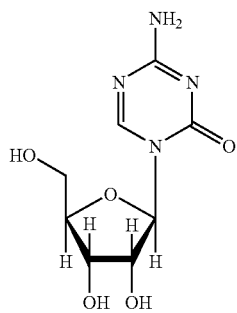

The 1,3,5-triazine ring of 5-azacytidine has a particular sensitivity to water (see J. A. Beisler, J. Med. Chem., 21, 204 (1978)), undergoing a reversible opening step to form the primary hydrolysis product, N-formylguanylribosylurea, with an equilibrium constant of 0.58+/−0.03 between pH 5.6 and 8.5, followed by an irreversible formation of the secondary hydrolysis product, guanylribosylurea.

The instability of the 1,3,5-triazine ring in water has made the determination of 5-azacytidine in plasma a challenge. For example, Rustum & Hoffman, J. Chromatog. 421: 387–391 (1987) show that even at −60° C., 5-azacytidine in plasma is unstable, with a 10% loss in 30 hours (see FIG. 3 of Rustum & Hoffman). At −10° C., the authors state that a 10% loss occurred in 2.5 hours, and at room temperature, a 10% loss occurred in 30 minutes. The authors conclude that 5-azacytidine determination in plasma must be performed as soon as possible after the blood draw because 5-azacytidine degrades rapidly even when the plasma is stored at low temperature.

The accurate determination of 5-azacytidine in plasma is of crucial importance because of the potential toxicity of the drug. Accurate determination would allow monitoring of 5-azacytidine administration in order to determine maximally therapeutic, but minimally toxic doses.

SUMMARY

The invention provides methods for preparing samples of plasma containing 5-azacytidine for quantitative analysis. Specifically, zinc sulfate and acetonitrile are added to plasma, mixed, and the resulting acetonitrile/plasma mixture is separated by centrifugation to yield an acetonitrile layer over a plasma layer. This process extracts the 5-azacytidine into the acetonitrile layer. The 5-azacytidine is stable when stored in the acetonitrile layer over the plasma layer for at least about 3 hours at about room temperature, and for at least about 4 days at about minus 70° C. If the acetonitrile layer is removed and evaporated to dryness, the 5-azacytidine in the resulting residue is stable for at least about 14 months at about minus 70° C. The 5-azacytidine in acetonitrile, or in the acetonitrile residue, may be quantitated using, for example, high-performance liquid chromatography with mass spectrometric detection.

BRIEF DESCRIPTION OF THE DRAWING

FIG. 1 illustrates a chromatogram for the analysis of a plasma sample containing 250 ng/mL of 5-azacytidine using high-performance liquid chromatography with mass spectrometric detection (LC/MS/MS).

DETAILED DESCRIPTION OF THE PREFERRED EMBODIMENTS

Figure 1A:
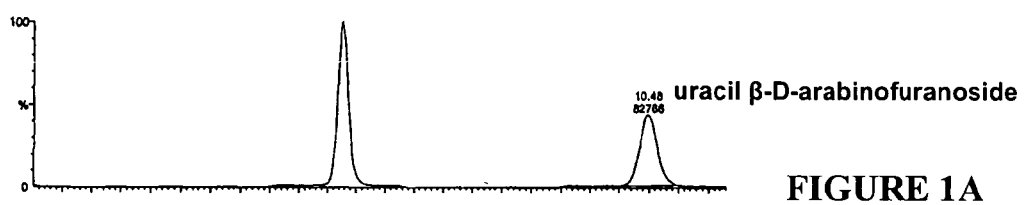
FIG. 1A shows the integrated uracil β-D-arabinofuranoside internal standard (IS) peak with a retention time of approximately 10.5 minutes.

In preferred embodiments of the invention, plasma from a patient undergoing 5-azacytidine treatment is separated from whole blood by centrifugation and then mixed with a solution of zinc sulfate in acetonitrile, preferably with a solution of at least 100 mg/mL zinc sulfate in acetonitrile. Preferably, the ratio of plasma to acetonitrile/zinc sulfate solution is less than or about equal to 1:20. Most preferably, about 100 μL of plasma is dispensed below the surface of about 2.0 mL of 200 mg/mL zinc sulfate in acetonitrile. Preferably, the plasma separation and the mixing of plasma with zinc sulfate and acetonitrile takes place within about 30 minutes of the blood draw. Most preferably, the whole blood and the plasma are stored on ice during this time.

The acetonitrile/zinc sulfate solution and plasma are mixed using, for example, a vortex mixer or other suitable mixing device. Preferably, the mixing is performed at about room temperature or lower, most preferably at about 5° C. or lower.

Following mixing, the resulting acetonitrile/plasma mixture is separated by centrifugation to partition the mixture into an acetonitrile layer over a plasma layer. Preferably, centrifugation is performed at about room temperature or lower, most preferably at about 5° C. or lower.

In one embodiment, the centrifuged acetonitrile/plasma mixture is then stored at about room temperature for at least about 3 hours prior to quantitating the 5-azacytidine. In another embodiment, the centrifuged acetonitrile/plasma mixture is stored at a temperature of about ≦minus 70° C. for at least about 4 days prior to quantitation of 5-azacytidine. After freezing, the acetonitrile/plasma mixture may be placed in dry ice, thereby permitting the centrifuged mixture to be transported conveniently to another location for 5-azacytidine determination.

In another embodiment, the acetonitrile layer is removed from the centrifuged acetonitrile/plasma mixture, most preferably by pipetting. The removed acetonitrile layer may then be stored at a temperature of about ≦minus 70° C. for at least about 4 days prior to quantitation of 5-azacytidine.

Alternatively, after freezing, the removed acetonitrile layer may be placed in dry ice, thereby permitting the removed acetonitrile layer to be transported conveniently to another location for 5-azacytidine determination.

In preferred embodiments, the acetonitrile layer is removed from the centrifuged acetonitrile/plasma mixture, most preferably by pipetting, and the acetonitrile layer is then evaporated prior to storage. The resulting residue may be stored at a temperature of about ≦minus 70° C. for at least about 14 months prior to quantitating the 5-azacytidine. Evaporation of the acetonitrile may be achieved, for example, using a vacuum evaporator.

The 5-azacytidine in the stored samples may be quantitated using any suitable technique known in the art. For example, high-performance liquid chromatography with a suitable detection method may be used to quantitate 5-azacytidine. In preferred embodiments, high-performance liquid chromatography with mass spectrometric detection (LC/MS/MS) is used to quantitate 5-azacytidine.

When samples prepared according to the foregoing methods are analyzed using LC/MS/MS, the measured 5-azacytidine concentration is within ±20% of the initial concentration of 5-azacytidine in the plasma sample (see Examples below). Thus, the foregoing methods allow accurate and precise quantification of 5-azacytidine in plasma.

The methods of the invention permit a significant time interval between the initial processing of the whole blood sample and the time of 5-azacytidine determination. The initial processing steps, comprising plasma separation and the addition of zinc sulfate and acetonitrile, are conveniently performed at the site where blood is drawn from the patient and require only the most basic laboratory equipment e.g., pipettes, bench top centrifuges, etc. In addition, preparation of an acetonitrile residue may also take place at the site where the blood is drawn. Once an acetonitrile/plasma mixture or an acetonitrile residue has been prepared, the sample may then be sent to a second location for the 5-azacytidine determination. Samples may be conveniently shipped on dry ice to the second location, and may be further stored prior to 5-azacytidine determination. For example, according to the methods provided herein, an acetonitrile/plasma mixture may be prepared at the site where blood is drawn from the patient and then shipped on dry ice to an analysis site where it is further processed to yield an acetonitrile residue. Alternatively, the acetonitrile/plasma mixture may be processed to yield an acetonitrile residue at the site where blood is drawn, and the residue may be shipped on dry ice to the analysis site. At the analysis site, the residue may then be stored at about ≦minus 70° C. for at least about 14 months prior to 5-azacytidine determination.

EXAMPLES

The following examples are provided for illustrative purposes only and are not intended to limit the scope of the invention.

Example 1

Stability of 5-Azacytidine in Whole Blood

5-Azacytidine was added to whole blood at a concentration of either 30 ng/ml or 400 ng/ml. The samples were incubated at room temperature or on ice for 15 minutes, 30 minutes, 45 minutes, or 60 minutes prior to quantitation; an additional sample was quantitated immediately following 5-azacytidine addition (Time 0).

Figure 1B:
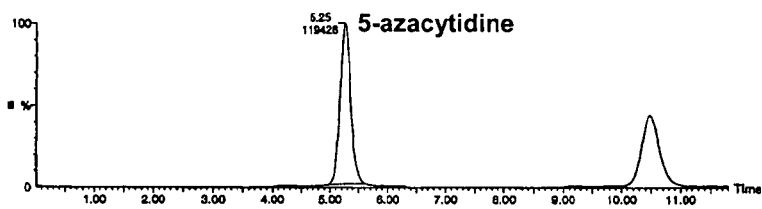
FIG. 1B shows the integrated 5-azacytidine peak with a retention time of approximately 5.3 minutes.

Quantitation was performed as follows. Whole blood (3.0 mL) was centrifuged to obtain plasma, and a 100 µL aliquot of the plasma was then added to a polypropylene tube containing at least 200 mg of zinc sulfate and 2.0 mL of acetonitrile by dispensing below the surface of the acetonitrile. Then, to each acetonitrile/plasma mixture, 25 µL of 500 ng/mL uracil β-D-arabinofuranoside was added as an internal standard (IS). The mixture was vortexed for 5 minutes, and then centrifuged for at least 5 minutes at 3000 rpm at 5° C. The acetonitrile layer was then transferred to a new polypropylene tube by pipetting. The acetonitrile layer was then evaporated using a turbo evaporator set at 45° C. After the sample was evaporated to dryness, 200 µL of ultra pure water was pipetted into the tube and the sample vortexed for 1 minute. The sample was then transferred to a polypropylene Gilson vial and centrifuged at 12,000 rpm for 2 minutes at room temperature. A 10 µL aliquot of the sample was then analyzed by high-performance liquid chromatography with mass spectrometric detection (LC/MS/MS). A representative chromatogram of a plasma sample spiked with 250 ng/mL 5-azacytidine along with the IS is presented in FIG. 1A–B. The retention time of 5-azacytidine is approximately 5.3 minutes and the retention time of the IS is approximately 10.5 minutes.

The concentration of 5-azacytidine was calculated from a calibration standard curve based on the respective analyte/IS peak area ratios. The line of best-fit for the calibration standards was calculated by weighted (1/y) quadratic regression based on analyte/IS peak area ratios for two replicates of seven calibration standards, using the Watson LIMS™ system (Innaphase Corp., Philadelphia, USA). The results are shown in Table 1 (CV=Coefficient of variation; SD=Standard Deviation; [5-aza]=concentration of 5-azacytidine; n.d.=not determined). Note that the 5-azacytidine concentrations shown in Table 1 are one half of the original plasma concentrations due to dilution of the sample.

TABLE 1

| [5-aza] (ng/mL) | Temp. | Time (mins) | Mean [5-aza] (ng/mL) | SD | % CV | % of Time 0 |
|---|---|---|---|---|---|---|
| 15 | Room Temp | 0 | 16.1 (N = 5) | 1.18 | 7.4 | — |
|  |  | 15 | 13.3 (N = 5) | 1.78 | 13.4 | 82.6 |
|  |  | 30 | 11.5 (N = 5) | 1.12 | 9.7 | 71.4 |
|  |  | 45 | 10.3 (N = 2) | n.d. | n.d. | 64.0 |
|  |  | 60 | n.d. | n.d. | n.d. | n.d. |
|  | Ice | 0 | 16.1 (N = 5) | 1.18 | 7.4 | — |
|  |  | 15 | 13.0 (N = 4) | 1.92 | 14.8 | 80.7 |
|  |  | 30 | 12.5 (N = 3) | 1.06 | 8.5 | 77.6 |
|  |  | 45 | 11.4 (N = 4) | 1.33 | 11.7 | 70.8 |
|  |  | 60 | 11.5 (N = 5) | 0.383 | 3.3 | 71.4 |
| 200 | Room Temp | 0 | 152.0 (N = 5) | 8.92 | 5.9 | — |
|  |  | 15 | 111.6 (N = 5) | 9.51 | 8.5 | 73.4 |
|  |  | 30 | 87.9 (N = 5) | 5.47 | 6.2 | 57.8 |
|  |  | 45 | 56.7 (N = 5) | 6.65 | 11.7 | 37.3 |
|  |  | 60 | 33.0 (N = 5) | 4.23 | 12.8 | 21.7 |
|  | Ice | 0 | 152.0 (N = 5) | 8.92 | 5.9 | — |
|  |  | 15 | 121.0 (N = 5) | 9.53 | 7.9 | 79.6 |
|  |  | 30 | 111.0 (N = 5) | 9.81 | 8.8 | 73.0 |
|  |  | 45 | 110.0 (N = 5) | 14.0 | 12.8 | 72.4 |
|  |  | 60 | 87.0 (N = 5) | 12.9 | 14.8 | 57.2 |

The results show that 5-azacytidine rapidly degrades in whole blood at room temperature, and at a slightly reduced rate when stored on ice.

Example 2

Stability of 5-Azacytidine Stored in Acetonitrile/Plasma Mixtures at Different Temperatures 5-azacytidine was added to whole blood at a concentration of either 30 ng/ml or 400 ng/ml. The whole blood (3.0 mL) was centrifuged to obtain plasma, and a 100 µL aliquot of the plasma was then added to a polypropylene tube containing at least 200 mg zinc sulfate and 2.0 mL acetonitrile by dispensing the plasma below the surface of the acetonitrile. The tube was vortexed for 5 minutes, and then centrifuged at approximately 3,000 rpm in a Beckman centrifuge for 5 minutes at 5° C. The acetonitrile/plasma mixtures were stored either for one freeze-thaw cycle (minus 70° C. for 4 days followed by room temperature (RT) for 5.5 hours) or at room temperature (RT) for approximately 3 hours. Additional samples were subjected to immediate 5-azacytidine determination without storage.

All 5-azacytidine determinations were performed as follows. To each acetonitrile/plasma mixture, 25 µL of a 500 ng/mL uracil β-D-arabinofuranoside solution was added as an internal standard (IS). The mixture was vortexed for 5 minutes, and then centrifuged for at least 5 minutes at approximately 3000 rpm at 5° C. The acetonitrile layer was then transferred to a new polypropylene tube by pipetting. The acetonitrile layer was then evaporated using a turbo evaporator set at 45° C. After the sample had evaporated to dryness, 200 µL of purified water was pipetted into the tube and the sample vortexed for 1 minute. The sample was then transferred to a polypropylene Gilson vial and centrifuged at 12,000 rpm for 2 minutes at room temperature. A 10 µL aliquot of the sample was then analyzed by high-performance liquid chromatography with mass spectrometric detection (LC/MS/MS).

The concentration of 5-azacytidine was calculated from a calibration standard curve based on the respective analyte/IS peak area ratios. The line of best-fit for the calibration standards was calculated by weighted (1/y) quadratic regression based on analyte/IS peak area ratios for two replicates of seven calibration standards, using the Watson LIMS™ system (Innaphase Corp., Philadelphia, USA). The results are shown in Table 2 (CV=Coefficient of variation; SD=Standard Deviation; [5-aza]=concentration of 5-azacytidine).

TABLE 2

| [5-aza] (ng/mL) | Sample preparation | Mean [5-aza] (ng/mL) | SD | % CV | % of Fresh Prep |
|---|---|---|---|---|---|
| 30 | Fresh prep. | 30.2 (N = 6) | 2.07 | 6.9 | — |
|  | Freeze-thaw | 31.2 (N = 6) | 3.30 | 10.6 | 103.3 |
|  | 3 hours RT | 29.8 (N = 6) | 4.00 | 13.4 | 98.7 |
| 400 | Fresh prep. | 415 (N = 6) | 33.4 | 8.0 | — |
|  | Freeze-thaw | 367 (N = 6) | 30.8 | 8.4 | 88.4 |
|  | 3 hours RT | 371 (N = 6) | 10.8 | 2.9 | 89.4 |

The results indicate that 5-azacytidine is stable (mean response of stored samples is within ±20% of freshly prepared sample) in acetonitrile/plasma solution for at least 4 days at minus 70° C. with one freeze-thaw cycle of 5.5 hours at room temperature. The results also indicate that 5-azacytidine is stable (mean response of stored samples is within ±20% of freshly prepared sample) in acetonitrile/plasma solution for at least about 3 hours at room temperature.

Example 3

Stability of 5-Azacytidine Stored as an Acetonitrile Residue at Minus 70° C.

5-Azacytidine was added to plasma at a concentration of either 30 ng/ml or 400 ng/ml. A 100 µL aliquot of the plasma was then added to a polypropylene tube containing at least 200 mg zinc sulfate and 2.0 mL acetonitrile by dispensing the plasma below the surface of the acetonitrile. To each acetonitrile/plasma mixture, 25 µL of a 500 ng/mL uracil β-D-arabinofuranoside solution was added as an internal standard (IS). The tube was vortexed for 5 minutes, and then centrifuged for 5 minutes at approximately 3000 rpm in a Beckman centrifuge at 5° C. The acetonitrile layer was then transferred to a new polypropylene tube by pipetting. The acetonitrile layer was then evaporated using a turbo evaporator set at 45° C. to yield an acetonitrile residue.

The acetonitrile residue was then stored at minus 70° C. for the time periods specified in Table 3 below. At each time point, the 5-azacytidine in the acetonitrile residue was determined as follows. To each acetonitrile residue was added 200 µL of purified water via a pipette and the sample vortexed for 1 minute. The sample was then transferred to a polypropylene Gilson vial and centrifuged at 12,000 rpm for 2 minutes at room temperature. A 10 µL aliquot of the sample was then analyzed by high-performance liquid chromatography with mass spectrometric detection (LC/MS/MS).

The concentration of 5-azacytidine was calculated from a calibration standard curve based on the respective analyte/IS peak area ratios. The line of best-fit for calibration standards was calculated by weighted (1/y) quadratic regression based on analyte/IS peak area ratios for two replicates of seven calibration standards, using the Watson LIMS™ system (Innaphase Corp., Philadelphia, USA). The results are shown in Table 3 (CV=Coefficient of variation; SD=Standard Deviation; [5-aza]=concentration of 5-azacytidine).

TABLE 3

| [5-aza] (ng/mL) | Sample Storage | Mean [5-aza] (ng/mL) | SD | % CV | % of Time 0 |
|---|---|---|---|---|---|
| 30 | Time 0 | 30.1 (N = 6) | 2.30 | 7.6 | — |
|  | 7 Days | 28.2 (N = 6) | 1.5 | 5.3 | 93.7 |
|  | 14 Days | 29.3 (N = 6) | 5.64 | 19.2 | 97.3 |
|  | 4 Weeks | 27.1 (N = 6) | 1.99 | 7.3 | 90.0 |
|  | 15 Weeks | 30.3 (N = 6) | 2.28 | 7.5 | 100.7 |
|  | 6 Months | 31.7 (N = 6) | 2.13 | 6.7 | 105.3 |
|  | 14 Months | 33.4 (N = 5) | 1.42 | 4.2 | 111.0 |
| 400 | Time 0. | 382 (N = 6) | 25.3 | 6.6 | — |
|  | 7 Days | 377 (N = 6) | 21.9 | 5.8 | 98.7 |
|  | 14 Days | 350 (N = 6) | 26.1 | 7.5 | 91.6 |
|  | 4 Weeks | 365 (N = 5) | 23.1 | 6.3 | 95.6 |
|  | 15 Weeks | 397 (N = 6) | 43.2 | 10.9 | 103.9 |
|  | 6 Months | 372 (N = 5) | 17.6 | 4.7 | 97.4 |
|  | 14 Months | 443 (N = 5) | 16.5 | 3.7 | 115.9 |

The results indicate that 5-azacytidine is stable (mean response of stored samples is within ±20% of freshly prepared sample) for at least 14 months when stored as an acetonitrile residue at minus 70° C.

What is claimed is:

1. A method for preparing a sample of plasma containing 5-azacytidine for quantitative analysis of said 5-azacytidine, the method comprising:

a) mixing said plasma with acetonitrile and zinc sulfate;
b) separating the mixture from step a) by centrifugation; and
c) storing the centrifuged mixture from step b) at a temperature less than or equal to about room temperature for at least about 3 hours.

2. The method of claim 1, wherein the ratio of plasma to acetonitrile/zinc sulfate solution in step (a) is less than or about equal to 1:20 (v/v).

3. A method for quantitating 5-azacytidine in plasma comprising:
a) mixing said plasma with acetonitrile and zinc sulfate;
b) separating the mixture from step a) into an acetonitrile layer and a plasma layer by centrifugation;
c) storing the centrifuged mixture from step b) at a temperature less than or equal to about room temperature for at least about 3 hours; and
d) measuring the amount of 5-azacytidine in said acetonitrile layer using high-performance liquid chromatography.

4. The method of claim 3, wherein the ratio of plasma to acetonitrile/zinc sulfate solution in step (a) is less than or about equal to 1:20 (v/v).

5. A method for preparing a sample of plasma containing 5-azacytidine for quantitative analysis of said 5-azacytidine, the method comprising:
a) mixing said plasma with acetonitrile and zinc sulfate;
b) separating the mixture from step a) into an acetonitrile layer and a plasma layer by centrifugation;
c) removing at least a portion of said acetonitrile layer; and
d) evaporating said removed acetonitrile layer to yield a residue comprising 5-azacytidine.

6. A method for quantitating 5-azacytidine in plasma comprising:
a) mixing said plasma with acetonitrile and zinc sulfate;
b) separating the mixture from step a) into an acetonitrile layer and a plasma layer by centrifugation;
c) removing at least a portion of said acetonitrile layer;
d) evaporating said removed acetonitrile layer to yield a residue comprising 5-azacytidine; and
e) measuring the amount of 5-azacytidine in said residue.

7. The method of claim 6 wherein the residue of step d) is stored at about minus 70° C. for between about 3 hours and about 14 months prior to step e).

8. The method of claim 6 wherein 5-azacytidine is measured in step e) using high-performance liquid chromatography with mass spectrometric detection.

* * * * *